(12) United States Patent
Kluczynski

(10) Patent No.: US 9,335,257 B2
(45) Date of Patent: May 10, 2016

(54) TUNABLE DIODE LASER ABSORPTION SPECTROSCOPY WITH WATER VAPOR DETERMINATION

(71) Applicant: Rosemount Analytical Inc., Houston, TX (US)

(72) Inventor: Pawel Kluczynski, Skorzewo (PL)

(73) Assignee: Rosemount Analytical Inc., Houston, TX (US)

( * ) Notice: Subject to any disclaimer, the term of this patent is extended or adjusted under 35 U.S.C. 154(b) by 0 days.

(21) Appl. No.: 14/307,995

(22) Filed: Jun. 18, 2014

(65) Prior Publication Data

US 2014/0375995 A1 Dec. 25, 2014

Related U.S. Application Data

(60) Provisional application No. 61/837,386, filed on Jun. 20, 2013.

(51) Int. Cl.
| | |
|---|---|
| *G01N 21/00* | (2006.01) |
| *G01N 21/27* | (2006.01) |
| *G01J 3/42* | (2006.01) |
| *G01N 21/39* | (2006.01) |
| *G01J 3/433* | (2006.01) |

(52) U.S. Cl.
CPC . *G01N 21/27* (2013.01); *G01J 3/42* (2013.01); *G01J 3/433* (2013.01); *G01J 3/4338* (2013.01); *G01N 21/39* (2013.01); *G01J 2003/423* (2013.01)

(58) Field of Classification Search
CPC . G01N 21/39; G01N 21/3504; G01N 21/031; G01N 2021/399; G01J 3/42
USPC ......................................................... 356/437
See application file for complete search history.

(56) References Cited

U.S. PATENT DOCUMENTS

| 5,930,000 A | 7/1999 | Brand |
|---|---|---|
| 7,800,764 B2 | 9/2010 | Kluczynski |

(Continued)

OTHER PUBLICATIONS

Search Report and Written Opinion from International Application No. PCT/US2014/043170, date of filing: Jun. 19, 2014, date of mailing: Oct. 27, 2014. 9 pages.

*Primary Examiner* — Tarifur Chowdhury
*Assistant Examiner* — Md M Rahman
(74) *Attorney, Agent, or Firm* — Christopher R. Christenson; Kelly, Holt & Christenson, PLLC

(57) ABSTRACT

A gas absorption spectroscopy system and method are provided. A sealed chamber is provided with a reference gas having a known moisture concentration. An illumination source is disposed in the sealed chamber and is configured to generate an illumination beam. A measurement cell is coupled to the sealed chamber and is configured for exposure to a gas sample such that illumination travelling through the measurement cell passes through the gas sample. A process window is disposed between the sealed chamber and the measurement cell. The process window is configured to receive the illumination beam from the illumination source and reflect a first portion of illumination while allowing a second portion of illumination to pass into the measurement cell. A reference detector is disposed to receive the first portion of illumination and provide a reference detector signal. A measurement detector is disposed to receive the second portion of illumination after the second portion of illumination has passed through the measurement cell and provide a measurement detector signal. A controller is coupled to the reference detector and the measurement detector and is configured to provide a compensated moisture output based on the reference detector signal and the measurement detector signal.

21 Claims, 3 Drawing Sheets

(56) References Cited

U.S. PATENT DOCUMENTS

| | | | |
|---|---|---|---|
| 8,164,748 B1* | 4/2012 | Flanders et al. | 356/300 |
| 2006/0011844 A1* | 1/2006 | Oka et al. | 250/343 |
| 2008/0179530 A1* | 7/2008 | Liu et al. | 250/343 |
| 2013/0135619 A1 | 5/2013 | Hirata et al. | |

* cited by examiner

TUNABLE DIODE LASER ABSORPTION SPECTROSCOPY WITH WATER VAPOR DETERMINATION

CROSS-REFERENCE TO RELATED APPLICATION

The present application is based on and claims the benefit of U.S. Provisional Patent Application Ser. No. 61/837,386 filed on Jun. 20, 2013, the content of which is hereby incorporated in its entirety.

BACKGROUND

Gas absorption spectroscopy generally measures the presence and/or concentration of a species of interest in a gas sample by passing a light beam through the sample and detecting the absorption at wavelengths of a particular spectral absorption feature of the species of interest. Generally, such a feature is an absorption line that represents the frequency of light corresponding to vibrational, rotational or electronic transitions of molecules of the gas of interest. Tunable diode lasers provide many advantages for such gas absorption spectroscopy measurements in that the lasers can be tuned to the center of a spectral feature and generate a narrow signal relative to the width of the spectral feature.

Laser absorption spectroscopy can thus offer high speed and relatively high precision capabilities for detecting a variety of trace gas species in gas samples at atmospheric pressures with relatively low cross sensitivity to other gas species or components. Tunable diode laser spectrometers are particularly suited to high sensitivity studies, in part, because they may be frequency-modulated to reduce low frequency laser noise and electronic noise. In general, a laser spectrometer will include a frequency tunable laser that generates an illumination output beam which is directed through a sample cell that contains a gas sample. The output beam is then directed to an optical detector and the signal of the optical detector is demodulated to obtain an absorption induced signal. This absorption induced signal can be used to identify one or more species of interest within the gas sample.

In some applications, it is important to detect trace moisture levels in a gas sample, such as natural gas, using a tunable diode laser absorption spectrometer. In such situations, the detection may be limited by spectral interference due to atmospheric moisture. Atmospheric, or any residual moisture present in the optical paths of the spectrometer, outside the sample cell may contribute to measurement error. Since the moisture level that may need to be detected within the gas sample is often below one part per million, atmospheric moisture levels ranging from 7,000-30,000 parts per million can generate significant measurement errors. Another important limitation in the detection of trace moisture levels in a gas sample is that the laser noise and the optical noise originating near the laser beam delivery optics may also limit the sensitivity and accuracy of the spectrometer.

Providing an apparatus and method that is able to adjust or otherwise compensate the trace moisture detection of a gas sample of interest based on atmospheric moisture and/or laser source noise/optical noise originating in the laser beam delivery optics would provide tunable diode laser absorption spectroscopy with improved accuracy and sensitivity.

SUMMARY

A gas absorption spectroscopy system and method are provided. A sealed chamber is provided with a reference gas having a known moisture concentration. An illumination source is disposed in the sealed chamber and is configured to generate an illumination beam. A measurement cell is coupled to the sealed chamber and is configured for exposure to a gas sample such that illumination travelling through the measurement cell passes through the gas sample. A process window is disposed between the sealed chamber and the measurement cell. The process window is configured to receive the illumination beam from the illumination source and reflect a first portion of illumination while allowing a second portion of illumination to pass into the measurement cell. A reference detector is disposed to receive the first portion of illumination and provide a reference detector signal. A measurement detector is disposed to receive the second portion of illumination after the second portion of illumination has passed through the measurement cell and provide a measurement detector signal. A controller is coupled to the reference detector and the measurement detector and is configured to provide a compensated moisture output based on the reference detector signal and the measurement detector signal.

DETAILED DESCRIPTION OF ILLUSTRATIVE EMBODIMENTS

Embodiments of the present invention generally provide a system and method that eliminate, or otherwise reduce, the influence of residual moisture present in the laser beam delivery volume as well as other sources of error such as the laser source noise and/or optical noise originating in the laser beam delivery optics. Additionally, residual moisture trapped in the laser beam delivery volume of the tunable diode laser absorption spectroscopy system can be used for stabilization and self-calibration of the system.

Figure 1:
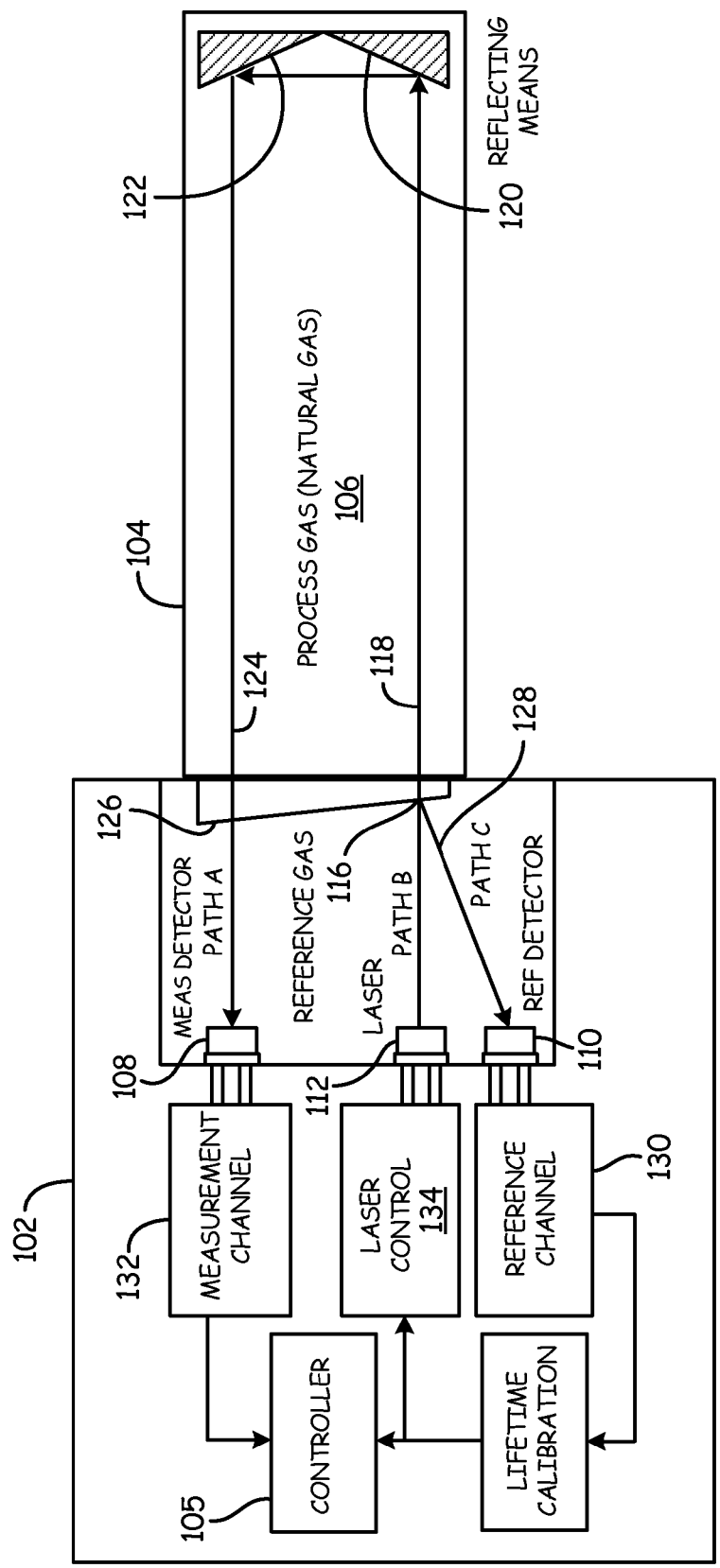
FIG. 1 is a diagrammatic view of a tunable diode laser absorption spectroscopy system in accordance with an embodiment of the present invention.

FIG. 1 is a diagrammatic view of a tunable diode laser absorption spectroscopy system in accordance with an embodiment of the present invention. System 100 includes laser head 102 coupled to measurement cell 104, which contains a process gas sample of interest 106. In the example shown, process gas sample of interest 106 is natural gas. System 100 employs a pair of detectors, measurement detector 108 and reference detector 110 in order to provide a number of important advantages. Reference detector 110, measurement detector 108, laser 112, and controller 105 are mounted within sealed laser head 102. Chamber 114 within sealed laser head 102 is filled with gas having a known moisture concentration (e.g., residual moisture). The laser beam generated by laser 112 travels from laser 112 to process window 116. Once reaching process window 116, a portion of the laser beam passes through window 116 into measurement cell 104. The portion of the laser beam passing through window 116 is illustrated diagrammatically at reference numeral 118. Beam 118 passes through the length of measurement cell 104 and then is reflected at reflectors 120, 122 into return beam 124 that passes out window portion 126 to measurement detector 108. As illustrated in FIG. 1, however, a portion of the beam emanating from laser 112 is also reflected at process window 116 into beam 128, which is detected by reference detector 110. Thus, a portion of the light from laser 112 is reflected off of process window 116 and follows Path C to reach reference detector 110. The optical path between the process window 126 and the measurement detector 108 (Path A) is selected, in one embodiment, to be identical to the optical path between process window 116 and reference detector 110 (Path C).

The double detector scheme described herein provides a number of advantages. First, a determination of the water vapor in the process gas (natural gas in the embodiment illustrated) can be obtained by processing of both measurement and reference detector signals. Additionally, the physical characteristics of the system allow for significant computational simplifications. Specifically, the signal from reference channel 130 (coupled to reference detector 110) is received by controller 105 and is subtracted from the signal received from measurement channel 132 (coupled to measurement detector 108) before further processing is done. This step allows controller 105 to monitor any changes in the laser characteristics independently of any process conditions. Further, corrections for any optical noise (interference patterns) originating from the laser and collimating optics in Path B can be performed simultaneously. This is normally a performance-limiting factor in many tunable diode laser absorption spectroscopy systems. Further still, contributions of the absorption by the reference gas (residual moisture) on the determination of water vapor content in the process (natural gas in the embodiment shown) can be eliminated, or otherwise reduced. This compensation is facilitated by the physical arrangement shown in FIG. 1 wherein the length of Path A is equivalent to that of Path C. Further, since the reference detector signal contains absorption information from a known reference gas, it can be used for controlling important laser parameters (such as laser frequency) as well as for the correction of any parameters that are important for maintaining the factory calibration of the instrument. In this way, the known residual moisture concentration trapped within laser head 102 can be used to provide lifetime calibration of the instrument.

Tunable diode laser (TDL) 112 is coupled to laser control module 134, which is coupled to controller 105 such that the frequency of the laser diode is tunable by controller 105. TDL 112, in one embodiment, is mounted on a bare TO-5 header. Light from TDL 112 is passed through a suitable beam shaping aperture and is weakly focused by an aspheric collimator lens (shown in FIG. 2). A small fraction of the beam is reflected off the wedged process window 116 to reference detector 110. After passing through measurement cell 104, the laser illumination is reflected off a concave mirror, situated in an end of measurement cell 104, back to the transceiver unit via the window portion 126. Finally, the returned laser illumination falls onto measurement detector 108. The distance between the laser and the collimator lens is chosen in order to create beam foci on both the reference and measurement detectors (108, 110, respectively). This arrangement reduces the number of optical components in the system, which reduction in turn reduces optical interference effects inside the transceiver unit (normally a limiting factor in any tunable diode laser system). An additional advantage of the arrangement shown in FIG. 1 is that the reference and measurement optical path lengths inside the transceiver unit are equal. While embodiments of the present invention can be practiced where they are not equal, providing equal path lengths provides for simplified compensation. In the embodiments shown in FIG. 1, laser head 102 is hermetically sealed and filled with a reference gas (e.g., nitrogen gas containing a small amount of water vapor).

The signal from reference detector 110 will contain information about the optical throughput in reference path (Path C in FIG. 1), reference gas absorption, laser frequency modulation and amplitude modulation characteristics as well as optical noise introduced by the laser assembly and the collimating lens. These are all relatively complex effects that are difficult to model and may, in fact, interact with one another in more complex relationships. However, the measurement detector signal, in turn, carries information about the optical throughput in the measurement path (Path A), the reference gas absorption, process gas absorption, laser frequency modulation and amplitude modulation characteristics as well as the optical noise introduced by the laser assembly and the collimating lens. Accordingly, a number of complex and difficult-to-model effects in the system can simply be subtracted by employing the signal from reference channel 130. Computation of the gas concentration inside measurement cell 104 is based on both reference detector 110 and measurement detector 108 according to the following. First, a normalization procedure is carried out in order to normalize the differences and optical throughputs between both channels 130, 132. The signal from reference channel 130 is used by itself to determine and control of important laser parameters, such as laser center frequency and frequency modulation characteristics. These parameters can be extracted from the reference gas absorption spectra. The difference between the normalized measurement and the reference signal is then used for extraction of gas concentration in the measurement cell. By doing so, the common constituents in the reference and measurement detector signals are eliminated, namely the reference gas absorption, laser amplitude modulation characteristics as well as the "common mode" optical noise originating in the laser assembly and the collimating lens. The latter decreases a demand for using special "low noise" collimating optics and laser assemblies, which is a very important factor in providing a practical system.

Figure 2:
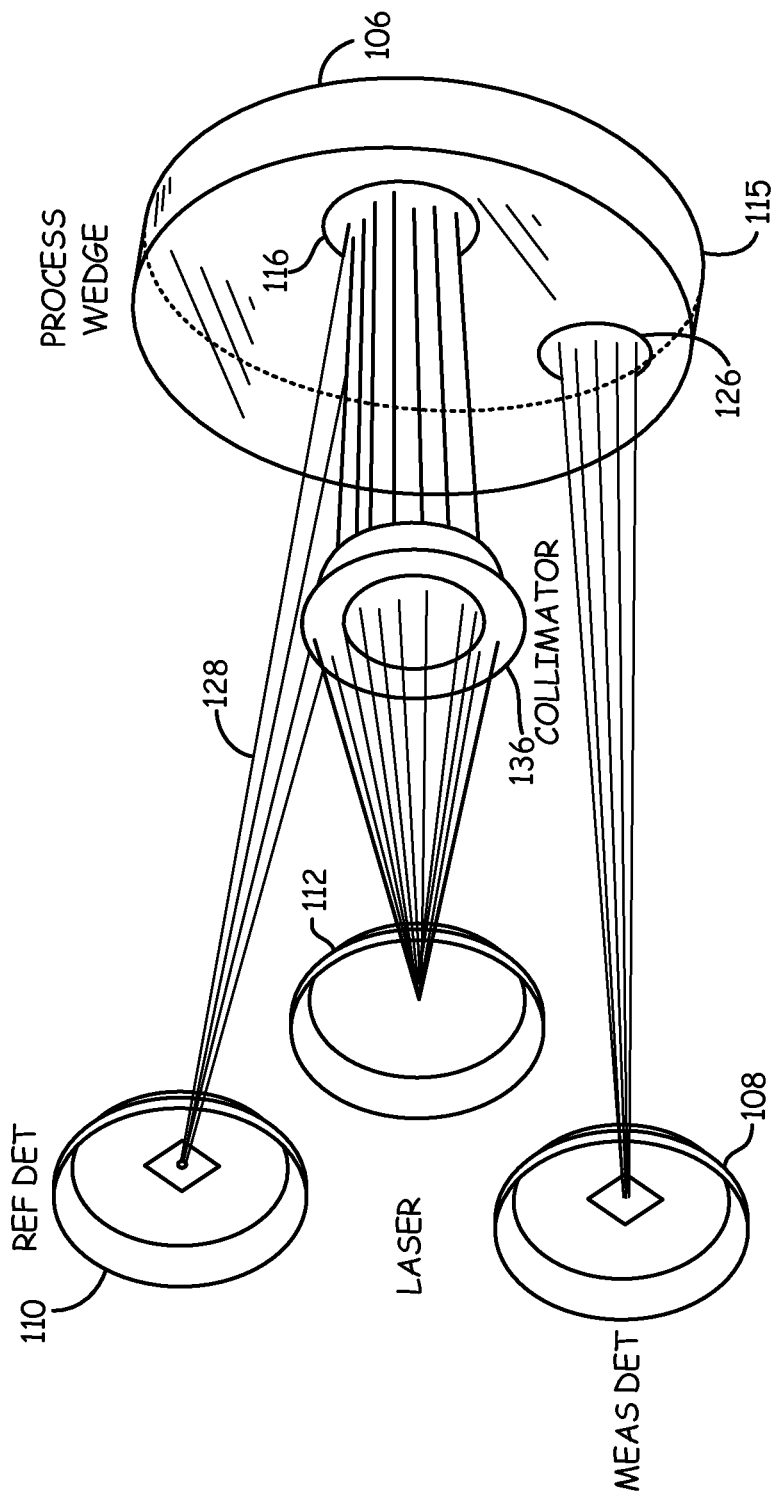
FIG. 2 is a ray tracing diagram illustrating the optical layout of a transceiver unit and corresponding detectors of a tunable diode laser absorption spectroscopy system in accordance with an embodiment of the present invention.

FIG. 2 is a ray diagram of an optical arrangement for a tunable diode laser absorption spectroscopy system in accordance with an embodiment of the present invention. As shown in FIG. 2, laser illumination is generated by laser 112 which is then collimated by collimator 136 before reaching process window 116 on process wedge 115. As shown in FIG. 2, the shape of process window 116 focuses the reflected beam 128 on reference detector 110. Additionally, a portion of the collimated illumination reaching process window 116 passes through process wedge 115 into the process gas 106. As described above with respect to FIG. 1, this beam passes through the length of the measurement cell and is reflected and returned through process window 126, which focuses the returned beam on measurement detector 108.

Figure 3:
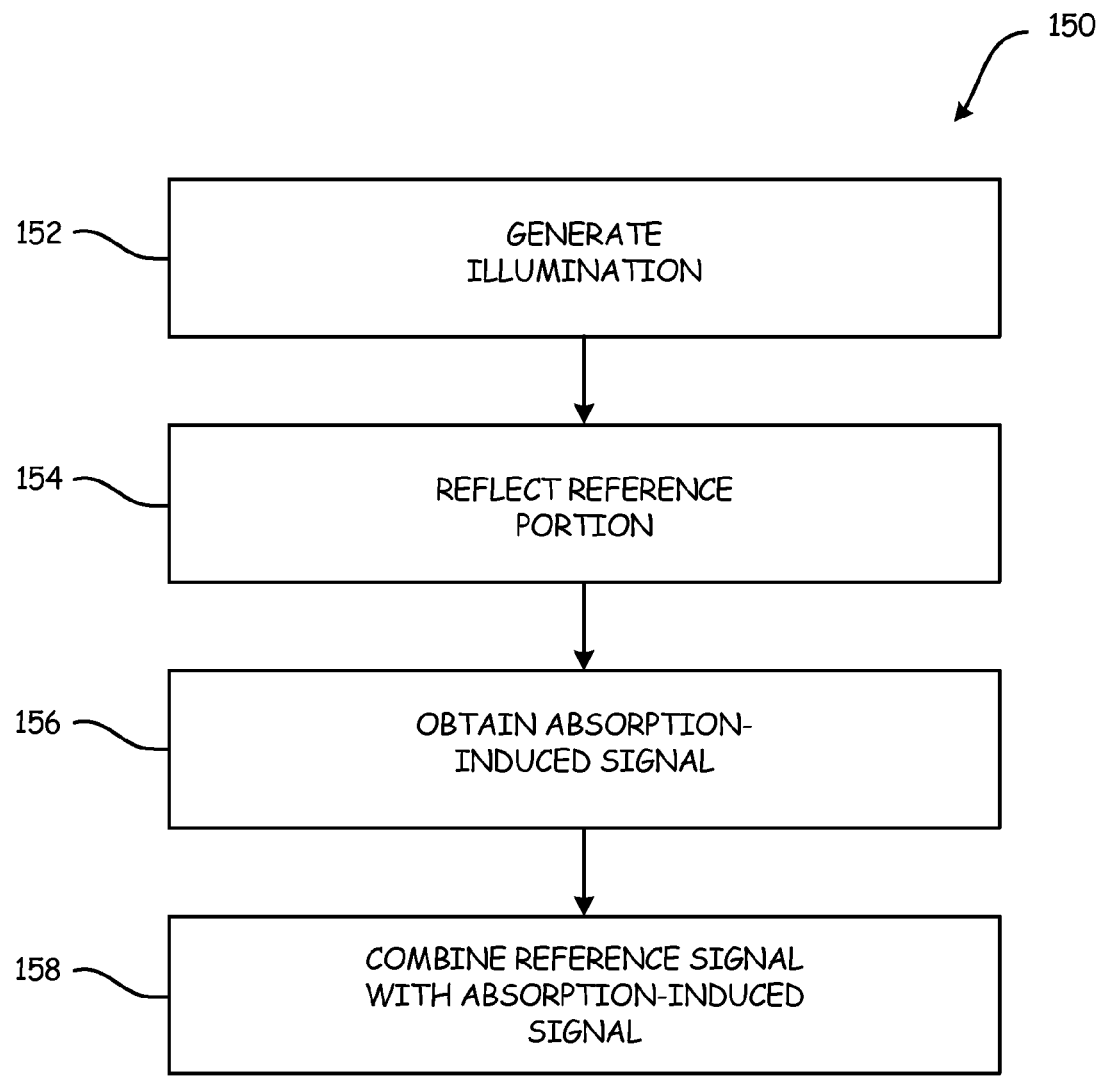
FIG. 3 is a flow diagram of a method of detecting trace moisture in a gas sample using a tunable diode laser absorption spectroscopy system in accordance with an embodiment of the present invention.

FIG. 3 is a flow diagram of a method of detecting trace moisture in a gas sample using a tunable diode laser absorption spectroscopy system in accordance with an embodiment of the present invention. Method 150 begins at block 152 where illumination is generated within a sealed enclosure having a known moisture composition. In one embodiment, the illumination is laser illumination generated by a tunable diode laser, such as TDL 112, described above. At block 154, a portion of the illumination generated at block 152 is reflected by a process window to a reference detector. The illumination reflected by the process window does not pass into a measurement cell, such as measurement cell 104. Instead, the reflected illumination only passes within the sealed enclosure having the known moisture composition. The signal of the reference detector is thus indicative of a number of variables relative to the sealed enclosure, laser frequency and amplitude modulations, et cetera. This signal can provide a wealth of useful information that can be used to control or otherwise set a number of parameters of the system. For example, the laser frequency can be controlled, at least in part, based on the reference detector signal. Additionally, or alternatively, the frequency modulation of the laser can be determined based on the reference detector signal.

At block 156, a portion of the illumination generated at block 152 passes through the process window into the measurement cell. In accordance with known principles, the illumination interacts with gas inside the measurement cell. When the illumination passing through the measurement cell reaches its respective detector, the measurement detector produces an absorption-induced signal. However, the absorption induced signal may also have a number of undesirable effects caused by residual moisture in the optical path, environmental moisture, and common mode optical noise. However, all of these undesirable effects are also present in the reference detector signal. At block 158, the reference detector signal is subtracted from the absorption-induced signal to provide a compensated moisture output.

Although the present invention has been described with reference to preferred embodiments, workers skilled in the art will recognize that changes may be made in form and detail without departing from the spirit and scope of the invention. While embodiments of the present invention have generally been described with respect to a controlled amount of a gas of interest (water vapor) sealed within a laser head for lifetime calibration, additional or alternative gases of interest could also be stored within the laser head as long as the absorption spectra of such reference gases could be disambiguated from one another. In this way, measurement head 102 could have lifetime calibration for a plurality of different gases of interest.

What is claimed is:

1. A gas absorption spectroscopy system comprising:
 a sealed chamber having a reference gas with a known moisture concentration therein;
 an illumination source disposed in the sealed chamber and configured to generate an illumination beam;
 a measurement cell coupled to the sealed chamber and configured for exposure to a gas sample such that illumination travelling through the measurement cell passes through the gas sample;
 a window disposed between the sealed chamber and the measurement cell, the window being configured to receive the illumination beam from the illumination source and reflect a first portion of illumination while allowing a second portion of illumination to pass into the measurement cell;
 a reference detector disposed to receive the first portion of illumination and provide a reference detector signal containing absorption information from the reference gas;
 a measurement detector disposed to receive the second portion of illumination after the second portion of illumination has passed through the measurement cell and provide a measurement detector signal; and
 a controller coupled to the reference detector and the measurement detector, the controller being configured to provide a compensated moisture output based on the reference detector signal and the measurement detector signal.

2. The gas absorption spectroscopy system of claim 1, wherein the window is configured to focus the reflected first portion on the reference detector.

3. The gas absorption spectroscopy system of claim 1, wherein the window is configured to focus the second portion of illumination on the measurement detector.

4. The gas absorption spectroscopy system of claim 1, wherein the controller is configured to subtract the reference detector signal from the measurement detector signal.

5. The gas absorption spectroscopy system of claim 1, wherein the illumination source is a tunable diode laser.

6. The gas absorption spectroscopy system of claim 5, and further comprising laser control circuitry coupling the tunable laser diode to the controller.

7. The gas absorption spectroscopy system of claim 6, wherein the controller is configured to select at least one operating parameter of the tunable diode laser based on the reference detector signal.

8. The gas absorption spectroscopy system of claim 7, wherein the at least one operating parameter is wavelength.

9. The gas absorption spectroscopy system of claim 7, wherein the at least one operating parameter is frequency modulation.

10. The gas absorption spectroscopy system of claim 1, wherein the system has lifetime calibration for moisture detection.

11. The gas absorption spectroscopy system of claim 10, wherein the system has lifetime calibration for at least one additional species of interest.

12. The gas absorption spectroscopy system of claim 1, wherein a ray path length from the window to the reference detector is equal to a ray path length from the window to the measurement detector.

13. A method of detecting moisture in a gas sample using tunable laser absorption spectroscopy, the method comprising:
 providing a sealed chamber having a known reference gas therein;
 providing an illumination source disposed in the sealed chamber and generating illumination in a sealed chamber with the illumination source;
 providing a measurement cell coupled to the sealed chamber and configured for exposure to a gas sample such that illumination travelling through the measurement cell passes through the gas sample;
 providing a window disposed between the sealed chamber and the measurement cell, the window being configured to receive the illumination beam from the illumination source and reflect a first portion of illumination while allowing a second portion of illumination to pass into the measurement cell;
 providing a reference detector disposed to receive the first portion of illumination and provide a reference detector signal containing absorption information from the reference gas;
 providing a measurement detector disposed to receive the second portion of illumination after the second portion of illumination has passed through the measurement cell and provide a measurement detector signal; and
 providing a controller coupled to the reference detector and the measurement detector, the controller being configured to provide a compensated moisture output based on the reference detector signal and the measurement detector signal.

14. The method of claim 13, wherein providing the compensated sample moisture content includes subtracting a signal from the reference detector from a signal from the measurement detector.

15. The method of claim 13, wherein reflecting first the portion includes focusing the reflected portion on the reference detector.

16. The method of claim 13, wherein the second portion of the generated illumination is reflected at an end of the measurement cell back to the window.

17. The method of claim 16, wherein the window is configured to focus the second illumination on the measurement detector.

18. The method of claim 13, wherein the illumination is laser illumination.

19. The method of claim 18, wherein at least one operating parameter of the laser illumination is controlled based on the reference detector signal.

20. The method of claim 18, wherein the operating parameter is wavelength.

21. The method of claim 18, wherein the operating parameter is frequency modulation.

* * * * *

UNITED STATES PATENT AND TRADEMARK OFFICE
CERTIFICATE OF CORRECTION

| | |
|---|---|
| PATENT NO. | : 9,335,257 B2 |
| APPLICATION NO. | : 14/307995 |
| DATED | : May 10, 2016 |
| INVENTOR(S) | : Pawel Kluczynski |

Page 1 of 1

It is certified that error appears in the above-identified patent and that said Letters Patent is hereby corrected as shown below:

In the Claims

Column 7, Lines 5-6:

"first" and "the" are misplaced, it should read "reflecting the first portion"

Signed and Sealed this
Second Day of August, 2016

Michelle K. Lee
*Director of the United States Patent and Trademark Office*